(12) United States Patent
Dreyfuss

(10) Patent No.: US 6,652,563 B2
(45) Date of Patent: Nov. 25, 2003

(54) SUTURE ANCHOR WITH INTERNAL SUTURE LOOP

(75) Inventor: Peter J. Dreyfuss, Naples, FL (US)

(73) Assignee: Arthrex, Inc., Naples, FL (US)

( * ) Notice: Subject to any disclaimer, the term of this patent is extended or adjusted under 35 U.S.C. 154(b) by 0 days.

(21) Appl. No.: 10/137,436

(22) Filed: May 3, 2002

(65) Prior Publication Data

US 2003/0065361 A1 Apr. 3, 2003

Related U.S. Application Data

(60) Provisional application No. 60/326,214, filed on Oct. 2, 2001.

(51) Int. Cl.$^7$ .............................................. A61B 17/04
(52) U.S. Cl. ...................................................... 606/232
(58) Field of Search ........................... 606/232, 60, 72, 606/73, 65, 222, 223, 224, 225, 226, 227

(56) References Cited

U.S. PATENT DOCUMENTS

| | | | |
|---|---|---|---|
| 5,037,422 A | * 8/1991 | Hayhurst et al. | 606/72 |
| 5,046,513 A | * 9/1991 | Gatturna et al. | 128/898 |
| 5,141,520 A | * 8/1992 | Goble et al. | 606/232 |
| 5,156,616 A | * 10/1992 | Meadows et al. | 606/232 |
| 5,207,679 A | * 5/1993 | Li | 606/72 |
| 5,571,139 A | * 11/1996 | Jenkins, Jr. | 606/232 |
| 5,584,835 A | 12/1996 | Greenfield | |
| 5,782,864 A | * 7/1998 | Lizardi | 606/232 |
| 5,849,004 A | 12/1998 | Bramlet | |
| 5,964,783 A | * 10/1999 | Grafton et al. | 606/232 |
| 6,027,523 A | * 2/2000 | Schmieding | 606/232 |

FOREIGN PATENT DOCUMENTS

| WO | WO 00/13601 | 3/2000 |
|---|---|---|
| WO | WO 02/21998 A2 | 3/2002 |

* cited by examiner

Primary Examiner—Michael J. Milano
Assistant Examiner—D. Jacob Davis
(74) Attorney, Agent, or Firm—Dickstein Shapiro Morin & Oshinsky, LLP

(57) ABSTRACT

A suture anchor has a suture loop that is disposed internally within the suture anchor. The suture loop extends through a substantial length of the anchor body with the ends of the suture loop secured at the distal end of the anchor and the proximal end of the loop being flush with or recessed just below the proximal surface of the proximal end of the anchor. The anchor body is threaded and has a tapered distal portion. The proximal end portion of the suture anchor body has a hexagonally shaped opening to accept a hexagonal drive head. The peripheral surface defining hexagonally shaped opening is rounded and smooth to prevent abrading sutures placed in contact therewith.

15 Claims, 3 Drawing Sheets

SUTURE ANCHOR WITH INTERNAL SUTURE LOOP

This application claims the benefit of U.S. Provisional Patent application Serial No. 60/326,214, filed Oct. 2, 2001.

BACKGROUND OF THE INVENTION

1. Field of the Invention

The present invention relates to an apparatus for anchoring surgical suture to bone. More specifically, the present invention relates to a suture anchor having an internal suture loop for receiving one or more strands of suture to anchor the suture to bone during arthroscopic surgery.

2. Description of the Related Art

When soft tissue tears away from bone, reattachment becomes necessary. Various devices, including sutures alone, screws, staples, wedges, and plugs have been used in the prior art to secure soft tissue to bone.

Recently, various types of threaded suture anchors have been developed for this purpose. Some threaded suture anchors are designed to be inserted into a pre-drilled hole. Other suture anchors are self-tapping.

U.S. Pat. No. 4,632,100 discloses a cylindrical threaded suture anchor. The suture anchor of the '100 patent includes a drill bit at a leading end for boring a hole in a bone, followed by a flight of threads spaced from the drill bit for securing the anchor into the hole created by the drill bit.

U.S. Pat. No. 5,370,662 discloses a suture anchor having threads which extend to the tip of the anchor. U.S. Pat. No. 5,156,616 discloses a similar suture anchor having an axial opening for holding a knotted piece of suture.

All of the above-noted suture anchors include structure for attaching the suture to the anchor. U.S. Pat. No. 4,632,100, for example, discloses a press-fitted disc and knot structure which secures the suture to the anchor. In other suture anchors, such as those disclosed in U.S. Pat. No. 5,370,662, the suture is passed through an eyelet located on the proximal end of the anchor. In the case of a bioabsorbable suture anchor, the suture may be insert molded into the anchor, as disclosed in U.S. Patent No. 5,964,783.

Problems can arise if the structure for attaching the suture fails, allowing the suture to become detached from the anchor. Also, the suture often is exposed to abrasion or cutting by sharp or rough areas along the walls of the bone canal into which the anchor is inserted.

Moreover, the eyelet or, in the case of U.S. Pat. No. 4,632,100, the axial opening for receiving the disc to which the suture is knotted, is formed as part of the drive head of the known suture anchors. Combining these two functions in one structure often tends to weaken the drive head.

In addition, various other modifications to the drive head often are employed in connection with suture attachment. For example, recessed grooves may be formed on opposite sides of the drive head to receive and protect the suture from abrasive areas of the suture anchor tunnel or to facilitate mating between the anchor to the driver. In such cases, the drive head often must be made of a larger diameter to recover the mechanical strength lost from the removal of material relating to the suture-attachment or suture-protection modifications.

Further, the prior art suture anchors having eyelets extending from the proximal ends require countersinking of the eyelet below the bone surface to avoid having the patient's tissue abrade against the exposed eyelet. As a result, suture attached to the eyelet is vulnerable to abrasion by the bony rim of the countersunk hole into which the suture anchor is installed. In addition, in biodegradable suture anchors, the suture eyelet can degrade rapidly, causing the suture to become detached from the anchor prematurely.

Accordingly, there is a need for a threaded suture anchor to which suture is secured effectively so as to prevent detachment of the suture. It is further desirable for such suture anchors to have eyelets that will not abrade tissue and which do not require countersinking.

SUMMARY OF THE INVENTION

The suture anchor of the present invention overcomes the disadvantages of the prior art discussed above by providing a threaded suture anchor having a suture loop disposed inside the body of the suture anchor. The suture anchor is made of a biocompatible metal, preferably a titanium alloy.

The proximal end surface of the threaded suture anchor of the present invention is preferably smooth and rounded to minimize suture abrasion, while the distal portion of the anchor is tapered to an elongated point to enable the anchor to be self-tapping. The proximal end portion of the suture anchor body has a hexagonally shaped opening to accept a hexagonal drive head.

The internal suture loop extends through a substantial length of the anchor body with the ends of the suture loop secured onto the distal end portion of the anchor and the proximal end of the loop being flush with or recessed just below the plane across the proximal face of the anchor.

Advantageously, suture attached to the anchor through the suture loop exits the suture anchor through a central bore in the anchor, which prevents suture abrasion by the wall of the bone tunnel into which the anchor is inserted.

Other features and advantages of the present invention will become apparent from the following description of the invention, which refers to the accompanying drawings.

DETAILED DESCRIPTION OF THE PREFERRED EMBODIMENT

Figure 1:
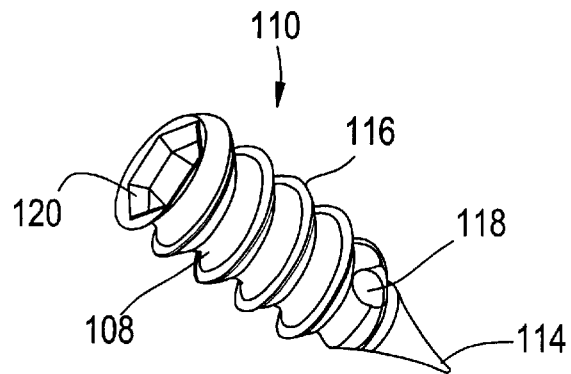
FIG. 1 is a perspective view of a first preferred embodiment of a suture anchor according to the present invention.
Figure 2:
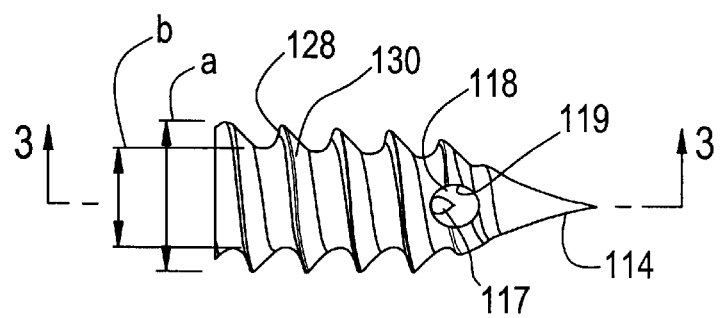
FIG. 2 is a side elevational view of the suture anchor shown in FIG. 1.

FIGS. 1 and 2 illustrate a suture anchor according to a first preferred embodiment of the present invention, indicated generally by reference numeral 110. In the preferred embodiment, body 108 of anchor 110 has a length of about 0.55 in., a major diameter "a" of about 0.21 in., and a minor diameter "b" of about 0.14 in. Suture anchor body 108 generally tapers to a narrow point 114 at the distal end thereof. In particular, the major diameter of the anchor body is generally constant along about two-thirds of the length of the body, whereupon the diameter of the anchor then tapers to a relatively sharp point, e.g., approximately 16°. The relatively sharp distal tip of anchor 110 enables the anchor to be installed without having to first drill a hole in the bone where the anchor 110 is to be installed.

Although such tapering is preferred, suture anchor 110 may be formed to have a less tapered shape, or even cylindrical shape, to accommodate different preferences of the surgeon and/or the application of the suture anchor. For example, the tapered distal end of the anchor may be formed to be more blunt, in which case it is necessary to provide a pre-formed hole in the bone prior to insertion of the suture anchor.

A continuous thread 116 wraps around the body 108 in a clockwise direction, as shown. Anchor 110 has about six flights of thread, with the angle of the proximal surface 128 of each thread being approximately one-third the angle of the distal surface 130 of each thread relative to the horizontal direction perpendicular to the longitudinal axis of the anchor, e.g., 15° versus 45°.

Figure 3:
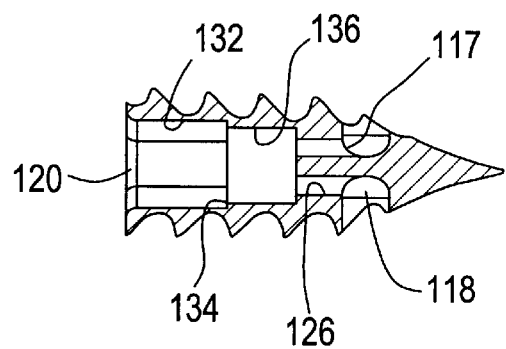
FIG. 3 is a longitudinal sectional view of the suture anchor shown in FIG. 2 through the plane III—III indicated therein.
Figure 4:
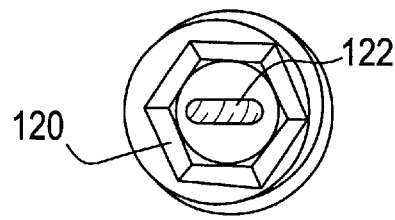
FIG. 4 is a proximal end view of the suture anchor of FIG. 1 including the internal suture loop therein.
Figure 5:
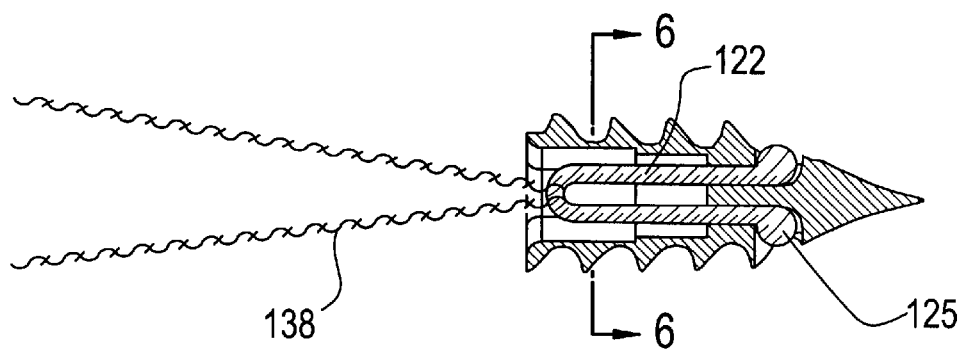
FIG. 5 is a cross sectional view of the suture anchor of FIG. 1 showing the internal suture loop therein, and having suture strands attached to the suture anchor through the internal suture loop.

As can be seen more clearly with reference to FIGS. 3 and 4, The proximal end portion of the anchor has a hexagonally shaped bore 132 having an opening 120 at the proximal end of anchor body 108 and extending into the anchor body approximately one-fourth of the length thereof. Prior art anchors have sharp edges around the drive opening, which is problematic in that sutures passing through the central opening at the proximal end of the anchor can be abraded by the sharp edges, thereby compromising the strength of the sutures. In the suture anchor of the present invention, the peripheral edges defining hexagonally shaped opening 120 is smooth and rounded outwardly with no sharp edges. Preferably, the opening 120 forms a slight lip curving around the diameter of the bore 132. Thus, sutures threaded through the anchor 110, as will be discussed below, will not become frayed upon being pressed or rubbed against the anchor at the proximal opening 120.

A cylindrical bore 136 having a diameter smaller than that of the hexagonally shaped bore 132 extends from the distal end of the hexagonally shaped bore 132 to a position roughly halfway along the length of anchor body 108. The transition between hexagonally shaped bore 132 and cylindrical bore 136 forms an annular shoulder 134, against which the distal end of a hex driver abuts when inserted into the hexagonally shaped bore 132 to drive the anchor into bone.

Figure 6:
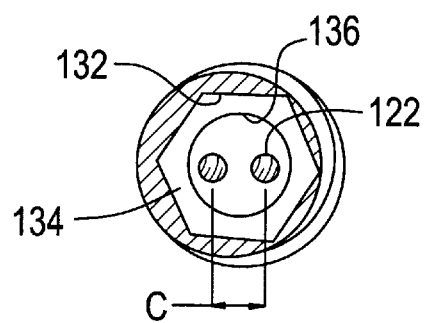
FIG. 6 is a cross sectional view through the suture anchor and suture loop of FIG. 5 through the plane VI—VI indicated therein.

Two longitudinal passageways 126 are formed in anchor body 108 distally to the cylindrical bore 136, extending from the distal end of bore 136 to two corresponding apertures 118 formed diametrically opposite to each other through the angled distal portion of suture anchor 110 near the distal tip 114. Referring to the cross-sectional view shown in FIG. 6, the preferred distance "c" between the centers of the two passageways 126 is about 0.55 in.

Apertures 118 each has an inner opening 117 defining the exit from the respective passageway 126, and widens to a larger, exterior opening 119 along the radial surface of anchor body 108. As can be seen in FIG. 2, apertures 118 extend through and interrupt the threads 116 around anchor body 108 at approximately one-third of the length of the anchor body from the distal end thereof. Due to the shape of apertures 118 and the angle at which apertures 118 intersect passageways 126, inner openings 117 is slightly oblong and may have an angle along the periphery thereof. So as to not abrade the suture loop which will be affixed therein (described below), it should be ensured during manufacture of the suture anchor body that the peripheral edges defining the inner openings 117 are smoothed and rounded.

An eyelet formed of a loop of suture 122 is disposed inside the body of suture anchor 110. The ends of the suture strand forming the loop are threaded through the longitudinal passageways 126 from the proximal opening 120 and pass into the apertures 118. Threading the ends of the suture through the passageways 126 and the apertures 118 may be facilitated by coating the ends of the suture (having a length longer than the length of the passageways 126) with a stiffening agent.

The proximal-most surface of the suture loop 122 is flush with or slightly recessed from the proximal opening 120, so that the suture loop does not project outside the body 108 of suture anchor 110. Preferably, the suture loop 122 is recessed between 0.05 to 0.14 in. from the plane across the suture anchor 110 at the proximal opening 120 thereof, as measured from the underside of the proximal-most point of the loop 122. The underside position corresponds to the depth into the bore 132 at which a suture strand inserted through the loop 122 would be attached to anchor 110.

To secure the suture loop onto anchor body 108, the ends of suture loop 122 are each tied in a knot 125, e.g., an overhand knot, and sealed with a biocompatible adhesive to permanently affix the knot. Knots 125 are then respectively inserted into the apertures 118 so that the knots are substantially entirely fitted within the space of the apertures 118. The smaller diameter of inner openings 117 of apertures 118 prevent the knots 125 from being pulled through into the interior of the anchor 110. Affixed in this manner, suture loop 122 has a pullout strength of 45 lbs. from the suture anchor 110.

Preferably, suture anchor 110 is formed of a hard biocompatible metal, such as a titanium alloy, but can be made of biocompatible materials other than metal. The material forming the suture loop 122 may be a #5 USP braided polyester or #2 fiberwire braid of polyester coated with a silicone elastomer.

The suture anchor according to the present invention need not be formed as a threaded device, but can also be formed as a tap-in type anchor. Also, the measurements, angles and ratios between the dimensions of the suture anchor may be varied from those described above so as to be suitable for the conditions and applications in which the suture anchor is to be used.

In manufacturing the suture anchor 110 in accordance with the present invention, the anchor body 108 is cast in a die, with the bores, passageways and apertures described above either being formed during the casting process or formed afterwards. If necessary, the distal tip 114 of the anchor 110 is trimmed to the desired length and the surfaces of the anchor are polished to the desired finish.

Figure 7:
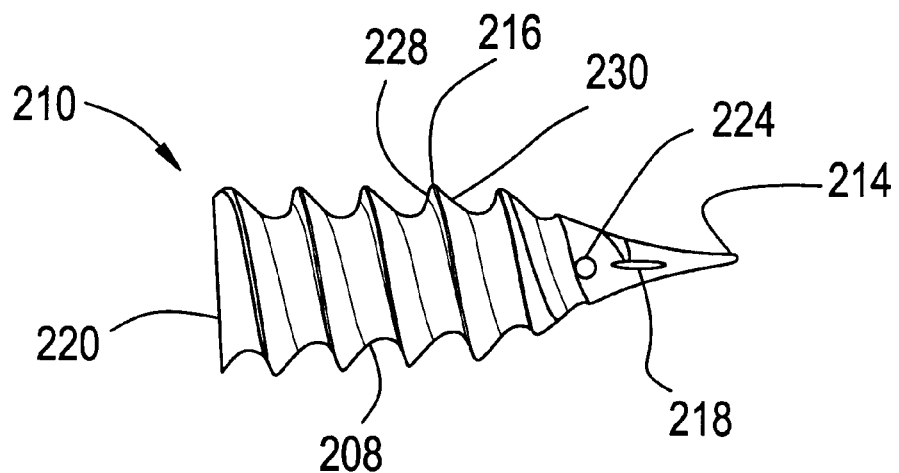
FIG. 7 is a side elevational view of a second preferred embodiment of a suture anchor according to the present invention.
Figure 8:
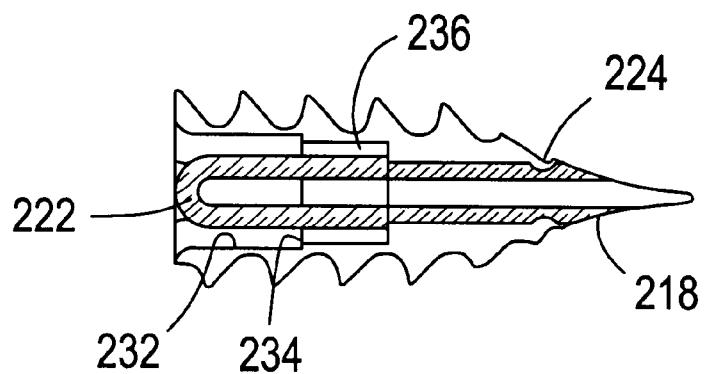
FIG. 8 is a longitudinal sectional view of the suture anchor shown in FIG. 7 and the internal suture loop therein through the plane VIII—VIII indicated in FIG. 7.

A second preferred embodiment of the suture anchor according to the present invention is shown in FIGS. 7 and 8. The structure of suture anchor 210 of this embodiment is substantially the same as the structure of suture anchor 110 except that the apertures 218 formed on the angled surface of the anchor body 208 is substantially smaller than the apertures 118 of the first embodiment described above. In particular, apertures 218 are formed at the distal end of passageways 226 just distally beyond the end of the thread 216.

Similarly to the embodiment described above, a suture loop 222 is provided inside suture anchor 210, except that the ends of suture loop 222 are secured in the anchor body 208, by crimping the body of the anchor 210 just proximally of the apertures 218 to form small detents 224, so that the ends of the suture loop 222 are pinched in place against the respective walls forming the passageways 226. The ends of the suture strands are then cut flush with the surface of the anchor. Formed in this manner, the suture loop may be provided with a pullout strength of up to about 90 lbs.

Preferably, the suture anchors according to the present invention are distributed to surgeons with one or more strands of suture 138 already threaded through the suture loop. Such sutures attached to the suture anchor through the internal suture loop must be able to slide smoothly through the slightly recessed loop. An example of a type of suture suitable for use in conjunction with the suture anchor and internal suture loop discussed herein is #2 braided polyester. If more than one suture strand is provided through the suture loop, each strand is preferably a different color, e.g., green, white, blue, etc.

Optionally, or if it becomes necessary due to the pre-threaded suture strands being accidentally removed from the suture loop, the user may be required to thread or re-thread the suture strands through the suture loop. In this case, threading a strand of suture through the suture loop may be facilitated if the ends of the suture strand are coated with a stiffening agent. Alternatively or additionally, a tool may be used to thread the suture strands and/or grasp the end of the suture after passing through the suture loop.

As mentioned above, the suture anchor of the present invention may be installed in the bone without the need to pre-drill a hole in the bone. The suture anchor is installed using a driver having a shaft having a hexagonal cross-section for at least a length equal to the length of the hexagonal bore 132, 232 from proximal opening 120, 220 to the shoulder 134, 234 inside the anchor 110, 210. The driver has a cannula extending through the entire length thereof, with openings at the proximal and distal ends thereof. Of course, the outer diameter of the hexagonal shaft is sized to fit inside the hexagonal bore in the anchor so as to be enabled to drive the same.

With the desired number of suture strands threaded through the suture loop in the suture anchor, the ends of the suture strands are threaded through the cannula in the hex driver from the distal end thereof and exiting from the proximal opening thereof. The distal end of the hexagonal shaft of the driver is then inserted into the proximal end of the anchor while the suture loop is inserted into the distal end opening of the driver. With the distal end of the driver abutting shoulder 134, 234 and the anchor positioned at the location at which it is to be installed, the hex driver is rotated to drive the anchor into the bone until the proximal surface of the anchor is flush with the surface of the bone.

Since it is not necessary for the proximal end of the anchor to be countersunk below the bone surface to prevent tissue abrasion by an exposed suture loop, as is required with prior art devices, the suture anchor of the present invention does not need to be inserted as far as the prior art anchors, while also avoiding abrasion of the sutures by the rim of the bone.

The suture anchor of the present invention provides greater pull-out strength of the suture loop than prior suture anchors. In addition, the suture loop of the present invention, being disposed inside the suture anchor, is protected from abrasion and degradation.

Although the present invention has been described in relation to particular embodiments thereof, many other variations and modifications and other uses will become apparent to those skilled in the art. Therefore, the present invention is to be limited not by the specific disclosure herein, but only by the appended claims.

What is claimed is:

1. A suture anchor comprising:

an anchor body having a central bore extending from an opening at the proximal end of the anchor body through a portion of the length thereof; and a suture loop disposed entirely in the central bore and having ends thereof affixed in the anchor body.

2. The suture anchor according to claim 1, wherein the anchor body is made of a metal material.

3. The suture anchor according to claim 1, wherein the suture loop is slightly recessed from the proximal opening of the anchor body.

4. The suture anchor according to claim 1, wherein the anchor body includes two channels formed from the distal end of the central bore to two respective apertures formed near the distal end of the anchor body.

5. The suture anchor according to claim 4, wherein the ends of the suture loop are affixed to the anchor body at the apertures formed near the distal end thereof by a knot formed at each respective end of the suture loop.

6. The suture anchor according to claim 5, wherein the knots formed at the ends of the suture loop are secured with a biocompatible adhesive.

7. The suture anchor according to claim 4, wherein the anchor body is made of a metal material.

8. The suture anchor according to claim 7, wherein the ends of the suture loop are affixed to the anchor body at the apertures formed near the distal end thereof by crimping the anchor body to pinch the ends of the suture loop in the respective apertures.

9. The suture anchor according to claim 1, further comprising at least one strand of suture threaded through the suture loop.

10. The suture anchor according to claim 1, wherein the anchor body is tapered.

11. The suture anchor according to claim 10, wherein the anchor body is tapered to a substantially narrow point.

12. The suture anchor according to claim 11, wherein the anchor body is threaded.

13. The suture anchor according to claim 12, wherein the anchor body is self-tapping.

14. The suture anchor according to claim 1, wherein the anchor body is threaded.

15. The suture anchor according to claim 1, wherein the central bore has a cross-sectional shape so as to accommodate a driver head for driving the suture anchor.

* * * * *